US010571375B2

(12) United States Patent
Nordstrom et al.

(10) Patent No.: US 10,571,375 B2
(45) Date of Patent: *Feb. 25, 2020

(54) HIGH PRECISION QUANTIFICATION OF SUB-VISIBLE PARTICLES

(71) Applicant: Intelligent Virus Imaging Inc., Southern Pines, NC (US)

(72) Inventors: Rickard Nordstrom Nordstrom, Tullinge (SE); Ida-Maria Sintorn, Sollentuna (SE); Lars Haag, Nykvam (SE)

(73) Assignee: Intelligent Virus Imaging Inc., Southern Pines, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/416,186

(22) Filed: May 18, 2019

(65) Prior Publication Data

US 2019/0271620 A1    Sep. 5, 2019

Related U.S. Application Data

(63) Continuation-in-part of application No. 16/277,393, filed on Feb. 15, 2019, now Pat. No. 10,345,207, which is a continuation of application No. 15/736,621, filed as application No. PCT/US2016/058011 on Oct. 21, 2016, now Pat. No. 10,247,648.

(60) Provisional application No. 62/269,464, filed on Dec. 18, 2015.

(51) Int. Cl.
| | | |
|---|---|---|
| *G01N 1/40* | (2006.01) | |
| *G01N 15/14* | (2006.01) | |
| *G01N 15/00* | (2006.01) | |

(52) U.S. Cl.
CPC .......... *G01N 1/4077* (2013.01); *G01N 15/14* (2013.01); *G01N 15/1468* (2013.01); *G01N 2001/4088* (2013.01); *G01N 2015/0038* (2013.01); *G01N 2015/1486* (2013.01)

(58) Field of Classification Search
CPC .. G01N 1/4077; G01N 15/14; G01N 15/1468; G01N 2015/1486; G01N 2015/0038
See application file for complete search history.

(56) References Cited

U.S. PATENT DOCUMENTS

| | | |
|---|---|---|
| 2002/0168757 A1 | 11/2002 | Kirk |
| 2003/0024877 A1 | 2/2003 | Amann et al. |
| 2010/0151446 A1 | 6/2010 | Homman |
| 2011/0041591 A1 | 2/2011 | Gupta |

*Primary Examiner* — Nicole M Ippolito
*Assistant Examiner* — Sean M Luck
(74) *Attorney, Agent, or Firm* — Fasth Law Offices; Rolf Fasth

(57) ABSTRACT

The method is for quantification of sub-visible particles. A filter membrane is provided that has a plurality of pores defined therethrough. The pores are sealed with a sealant such as glycine or poly-vinyl alcohol (PVA). A sample droplet, containing liquid and sub-visible particles, is applied onto the filter membrane. The liquid dissolves the sealant in pores disposed directly below the sample droplet. The liquid flows through the pores in which the sealant has been dissolved and the sub-visible particles remain on top of the filter membrane. The particles are enumerated in an electron microscope.

11 Claims, 9 Drawing Sheets

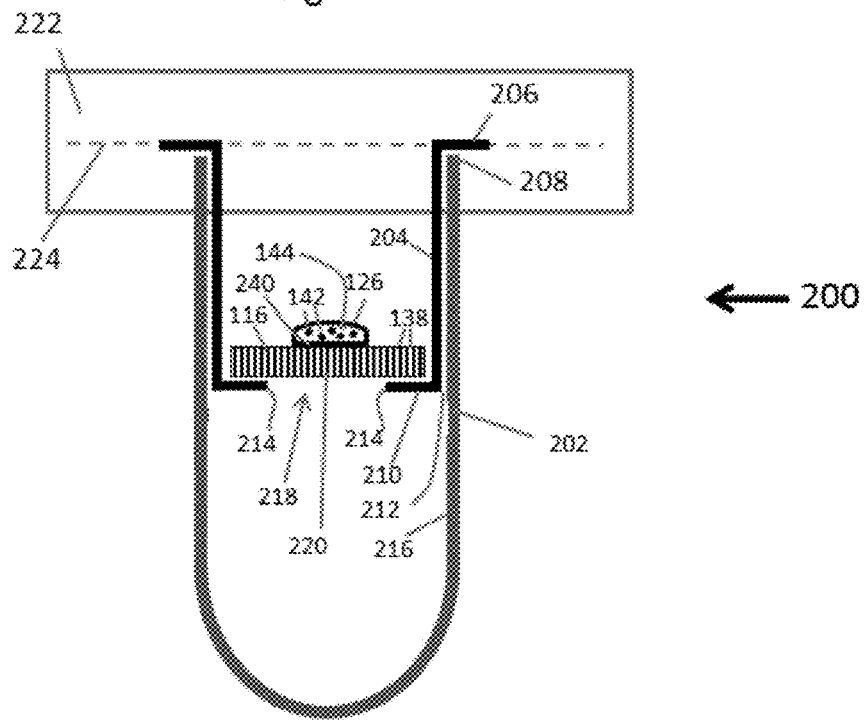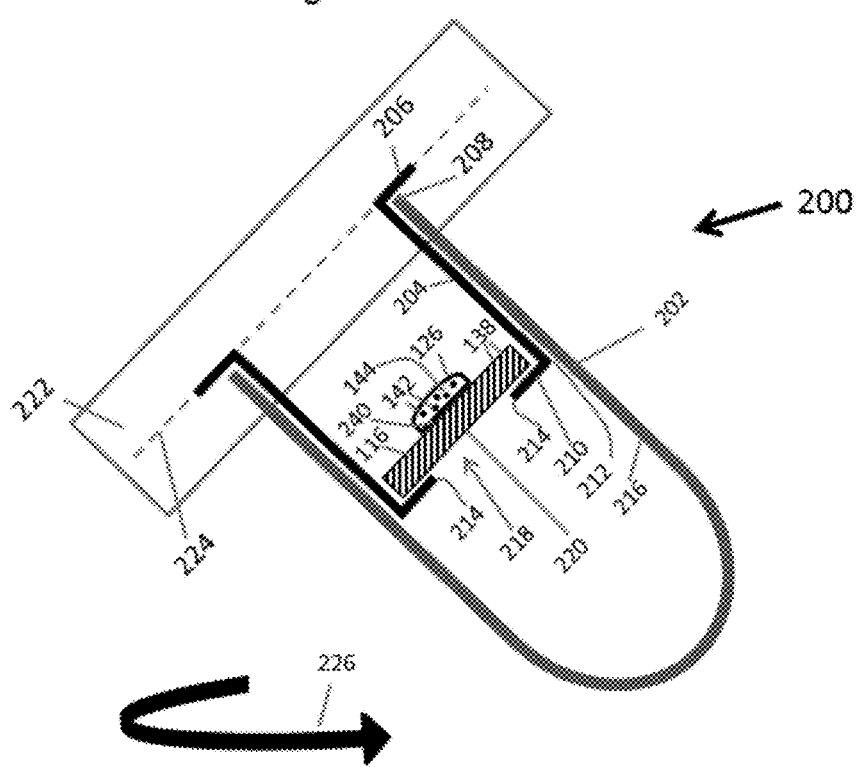

HIGH PRECISION QUANTIFICATION OF SUB-VISIBLE PARTICLES

PRIOR APPLICATIONS

This is a continuation-in-part patent application that claims priority from continuation application Ser. No. 16/277,393, filed on 15 Feb. 2019, that claims priority from U.S. patent application Ser. No. 15/736,621, filed on 14 Dec. 2017 that claims priority from PCT patent application no. PCT/US2016/058011, filed on 21 Oct. 2016 that claims priority from U.S. provisional patent application No. 62/269,465, filed on 18 Dec. 2015.

TECHNICAL FIELD

The present invention relates to a method for high precision quantification of sub-visible particles, such as micro-particles and/or nanoparticles, using microscopy such as scanning electron microscopy (SEM).

BACKGROUND AND SUMMARY OF THE INVENTION

A precise enumeration of the number of sub-visible particles such as virus particles, virus-like particles, inorganic and polymeric beads and other nanoparticles and micro-particles from liquid samples is important in many processes. For example, modified virus vectors are commonly used in gene therapy applications. The number of active vectors per mL (the infectious titer of the virus sample) can be determined using standard infectivity assays. However, by using the currently available methods, it is not possible to precisely determine the total number of particles, including non-infectious particles, in the sample. The ratio of infectious over non-infectious particles provides invaluable information about the quality and efficacy of the final gene therapy product and the upstream development processes.

One major limitation of the currently available techniques, such as quantitative flow cytometry (QFCM), is that the nanoparticles of interest are not directly detected. Instead, the number of bound probes to a population of nanoparticles is quantitated. Since the number of probes that binds per nanoparticle varies, the precision of the conventional indirect techniques is typically low and dependent on the affinity between the specimen and probe. A technique where the nanoparticle of interest could be directly detected would overcome this limitation. Moreover, if the technique would be able to visualize the particles at sufficient resolution, individual particles could be identified based on their size and morphology and thus be directly enumerated. Even particles within clusters could be enumerated and estimated. This is not possible by using the currently available affinity methods or light scattering-based techniques.

The novel high-precision direct particle method of the present invention may be used to enumerate both inorganic and organic sub-visible particles, such as nanoparticles, from liquid samples. One important feature is that the specimens are applied on a well-defined and measurable footprint. Another important feature is that the specimens are more evenly distributed than what has been possible before and this reduces the need for sampling and it is now possible to conduct the analysis at a resolution where the individual particles can easily be identified. The sub-visible particles are directly detected without the need for signal probes and can be visualized in normal two-dimensional images. The particle quantification SEM (pqSEM) method of the present invention is preferably based on low-vacuum filtering, scanning electron microscopy (SEM) or other electron microscopy techniques and image analysis. The present invention can be used with or without internal standards, of which an example would be National Institute of Standards and Technology (NIST) characterized polystyrene beads.

The present invention provides a solution to the above described problems. More particularly, the method is for quantification of sub-visible particles. A filter membrane is provided that has a plurality of pores defined therethrough. The filter membrane is in operational engagement with a vacuum chamber. The pores are sealed with a sealant. A sample droplet, containing a liquid with sub-visible particles, is applied onto the filter membrane. The liquid dissolves the sealant in the pores located directly below the sample droplet. The liquid flows through the pores in which the sealant has been dissolved and the sub-visible particles remain on top of the filter membrane. The filter membrane, with the particles disposed thereon, is moved to an electron microscope and enumerated in images acquired in the microscope.

The method further comprises the step of pre-mounting a filter assembly, containing the filter membrane, onto a SEM support.

The method further comprises the step of placing a mounting tape on the SEM support.

The method further comprises the step of providing the SEM support, having an elongate channel defined therein, using an injector containing the sample droplet, and aligning the injector on top of an elongate channel prior to depositing the sample droplet on the filter membrane.

The method further comprises the step of connecting the SEM support to a vacuum chamber connected to a vacuum source and subjecting the filter membrane to a suction force via the elongate channel.

The method further comprises the step of depositing the sample droplet onto the filter membrane without the sample droplet touching any outside edge of the filter membrane.

The method further comprises the step of the liquid only dissolving the sealant in the pores disposed directly below the sample droplet while the adjacent pores on the side of the droplet remain sealed with the sealant because the liquid has not been in contact with the sealant disposed in those pores.

The method further comprises the step of the sub-visible particles forming a defined and measurable footprint on the filter membrane and acquiring a series of images of the particles from an outside periphery of the footprint to the center of the footprint.

The method further comprises the step of counting the particles in the electron microscopy images acquired at a resolution where the particles are clearly visible—either manually or automatically using image analysis methods.

The method further comprises the step of estimating the total area of the footprint on the filter membrane in microscopy images covering the whole footprint (either one low-magnification image covering the whole footprint or several higher magnification sub-images of the footprint stitched together).

The method further comprises the step of calculating the total number of particles in the sample from the area of the whole footprint and the number of particles per area unit derived from images at a resolution high enough to clearly see single particles.

The method further comprises the step of possibly compensating for uneven radial particle distribution of the particles in the footprint for which information is derived from acquiring a series of images from the periphery of the footprint through the center at a high enough magnification to clearly see individual particles.

The method further comprises the step of calculating the concentration of particles in the solution using the total particle estimate from the footprint; the applied volume and dilution of the liquid sample.

The method further comprises the step of using a diluent of the liquid to dissolve the sealant in the pores located directly below the sample droplet. The specimen should be in a liquid form and the diluent should be compatible with the diluent and have the property of effectively dissolving the sealant that is being used.

The method further comprises the step of using glycine as the sealant. Other sealants that could be used include, but are not limited to, water-soluble polymers such as polyvinyl alcohol (PVA) or trehalose/sucrose-based sealants.

Additionally, the method is for quantification of sub-visible particles wherein a filter membrane is provided that has a plurality of pores defined therethrough. A dissolvable sealing layer is positioned on the filter membrane and a filter paper is placed below the filter membrane. A sample droplet, containing liquid and sub-visible particles, is applied onto the sealing layer. The liquid dissolves a region of the sealant layer disposed below the sample droplet. The liquid flows through the pores disposed below the region and into the filter paper and the sub-visible particles remain on top of the filter membrane. The filter paper provides a suction force to urge the liquid to flow through the pores in the region and the sub-visible particles are enumerated in an electron microscope.

The method further comprises the step of sealing the pores of the membrane with a dissolvable sealant.

The method also comprises the step of providing a sealant layer soluble by the sample liquid on top of the filter membrane. This sealing layer can be based on, for example, but not limited to: glycine, trehalose, sucrose, poly-vinyl alcohol (PVA), or other polymers.

In alternative, a container is provided that contains a filter membrane that has a plurality of pores defined therethrough. The pores are sealed with a sealant. A sample droplet, containing liquid and sub-visible particles, is applied onto the filter membrane. The liquid dissolving the sealant in pores disposed below the sample droplet. The container is rotated to create a centrifugal force that urges the liquid through the pores in which the liquid has dissolved and the sub-visible particles remain on top of the filter membrane. The sub-visible particles are then enumerated in an electron microscope.

The method further comprises the step of resting the filter membrane on a support disposed inside the container.

Additionally, the method comprises the step of placing the sample droplet on the filter membrane when the container is in an upright position and gradually moving the container to a horizontal position while rotating the container.

The method further comprises the step of rotating the container about a rotation axis at a top of the container.

The method further comprises the step of the liquid only dissolving the sealant in the pores disposed immediately below sample droplet while adjacent pores remain sealed with the sealant.

The method further comprises the step of using poly-vinyl alcohol (PVA) or any other suitable material as the sealant.

The method also comprises the step of applying the sample droplet onto the filter membrane without the sample droplet touching any outside edge of the filter membrane.

In an alternative embodiment, the method comprises the step of providing a container that contains a filter membrane that has a plurality of pores defined therethrough. A dissolvable sealing layer is positioned on the filter membrane. A sample droplet, containing liquid and sub-visible particles, is applied onto the sealing layer. The liquid dissolves a region of the sealant layer disposed below the sample droplet. The container is rotated to create a centrifugal force. The centrifugal force urges the liquid through the pores in the region which the liquid has dissolved and the sub-visible particles remain on top of the filter membrane. The sub-visible particles are then enumerated in an electron microscope.

BRIEF DESCRIPTION OF DRAWINGS

FIG. 7 is a cross-sectional schematic side view of an alternative embodiment of the present invention in a vertical position;

FIG. 8 is a cross-sectional schematic side view of the embodiment shown in FIG. 7 in a slanted rotating position;

DETAILED DESCRIPTION

Figure 1:
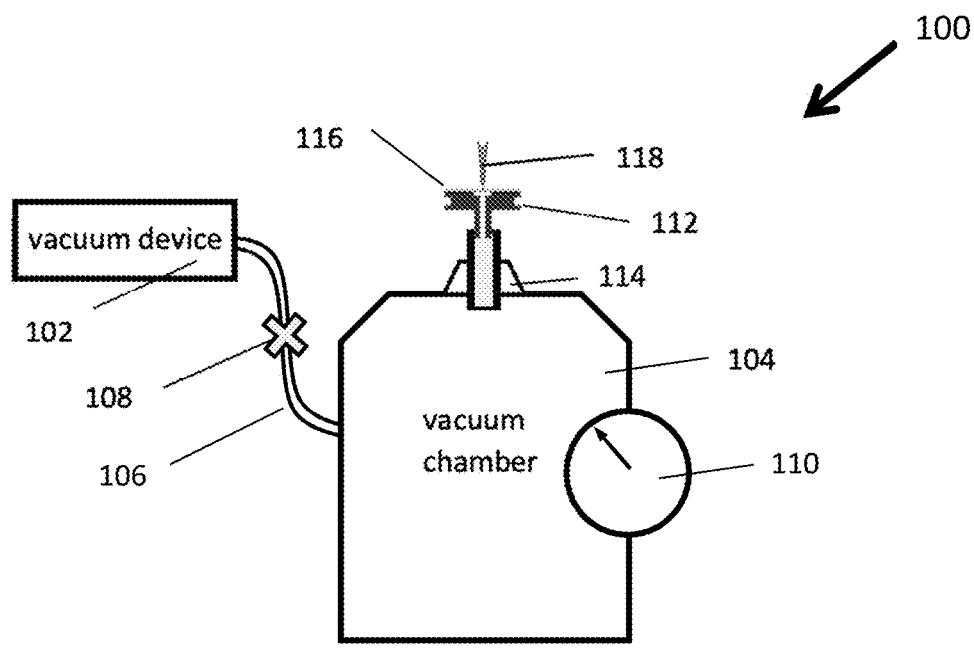
FIG. 1 is a schematic elevational side view of a vacuum device of the present invention.

The method of the present invention is described with reference to FIGS. 1-6. FIG. 1 is a schematic front view of a vacuum assembly 100 that has a vacuum device 102 connected to a vacuum chamber 104 via a tubing 106 extending therebetween. Preferably, the tubing 106 has a suitable valve such as a luer valve 108. A vacuum manometer 110 is in operative engagement with the vacuum chamber 104 to measure a vacuum pressure therein. A filter assembly 112 is mounted by a filter assembly mount 114 on top of the vacuum chamber 104. A filter membrane 116 is disposed on the filter assembly 112. An injector 118 is located above the filter membrane 116.

Figure 2:
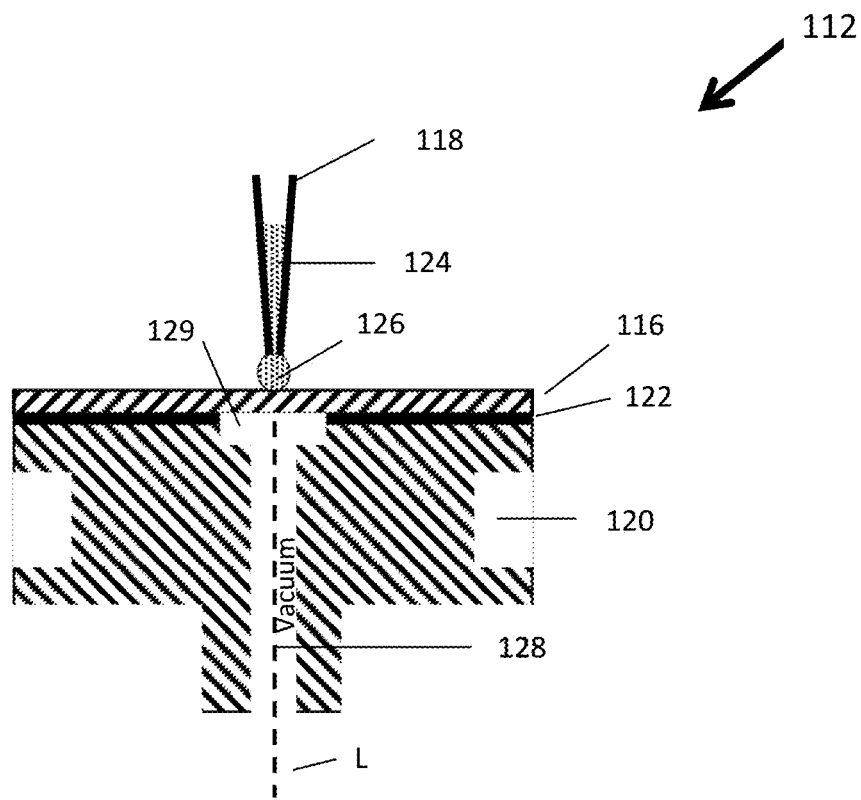
FIG. 2 is a schematic cross-sectional side view of the filter assembly.

FIG. 2 is a schematic cross-sectional view of the filter assembly 112. The entire analysis process of the present invention may be simplified by pre-mounting the filter membrane 116 onto the SEM support (alumina stub) 120 instead of doing it manually when the filter membrane 116 contains the sample/specimen to be analyzed and enumerated. The mounting may be done by simply drilling a hole in the SEM stub 120. The use of such a device minimizes the risk of losing specimen or damaging the filter membrane 116 during the previous setup in which the filter membrane 116 that contains the specimen is handled manually during the mounting onto the SEM stub 120. The details of the preparation of the filter membrane 116 are discussed below. Such a pqSEM analytical consumable device is relatively inexpensive to manufacture.

More particularly, the filter assembly 112 preferably has a modified SEM alumina stub 120 onto which a double-sided carbon mounting tape 122 is placed. The sealed porous filter membrane 116 is placed on top of the carbon mounting tape 122. The process of sealing the filter membrane 116 is described in detail below particularly with reference to FIGS. 5-6. The injector 118, that contains a specimen or sample 124 to be analyzed, is disposed or positioned above the filter membrane 116 and is used to deposit a sample droplet 126 onto the filter membrane 116. Because the stub 120 is sealingly connected to the filter assembly mount 114 that, in turn, is mounted on the vacuum chamber 104, there is vacuum inside the stub 120 so that the vacuum exerts a suction force on the filter membrane 116 from below the filter assembly 112. This is enabled because an elongated cavity or channel 128, defined inside the stub 120, is in fluid communication with the filter membrane 116 and the vacuum chamber 104. As described below, it is important that the injector 118 is correctly positioned above the filter membrane 116 so that when the sample droplet 126 is deposited onto the filter membrane 116, the sample droplet 126 is not in contact with edges of the filter membrane 116 and placed directly above an enlarged cavity portion 129 that is defined between channel 128 and the underside of the mounting tape 122. Preferably, the droplet 126 is placed at or near the center of the cavity portion 129 that is aligned with a longitudinal axis (L) that extends through the channel 128.

Figure 3A:
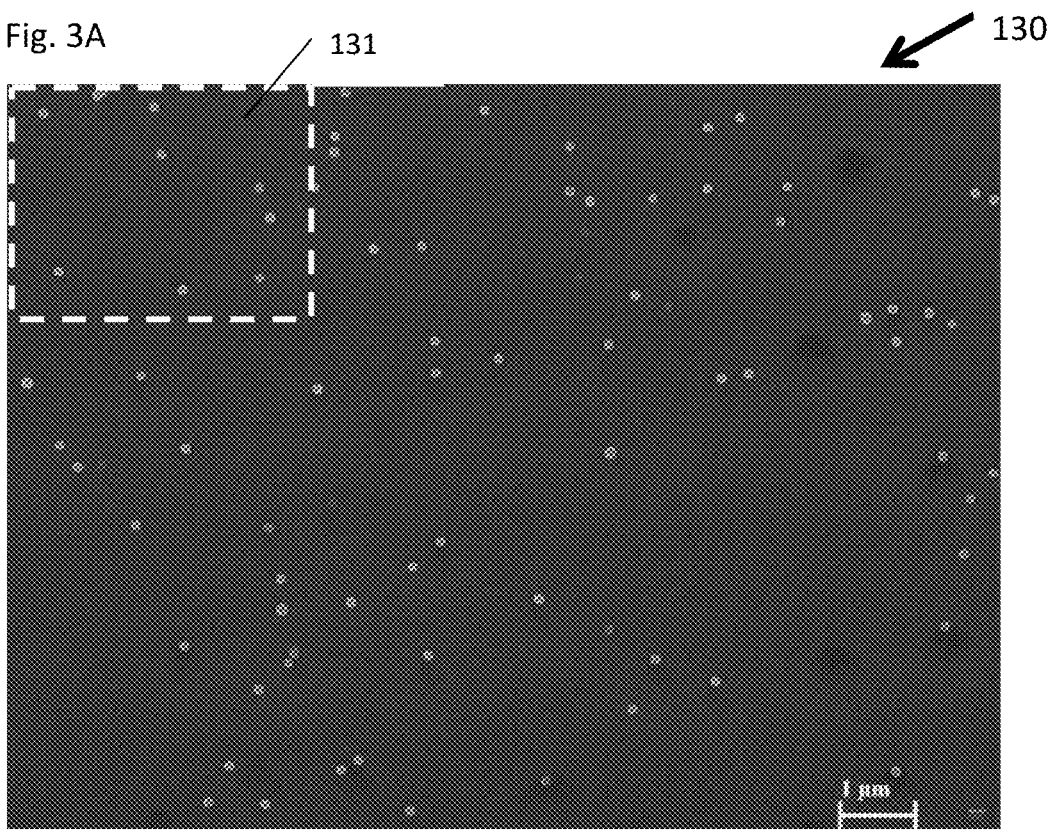
FIG. 3A is an unprocessed high magnification SEM image of polystyrene beads adhered to a poly-ether sulfone filter.
Figure 3B:
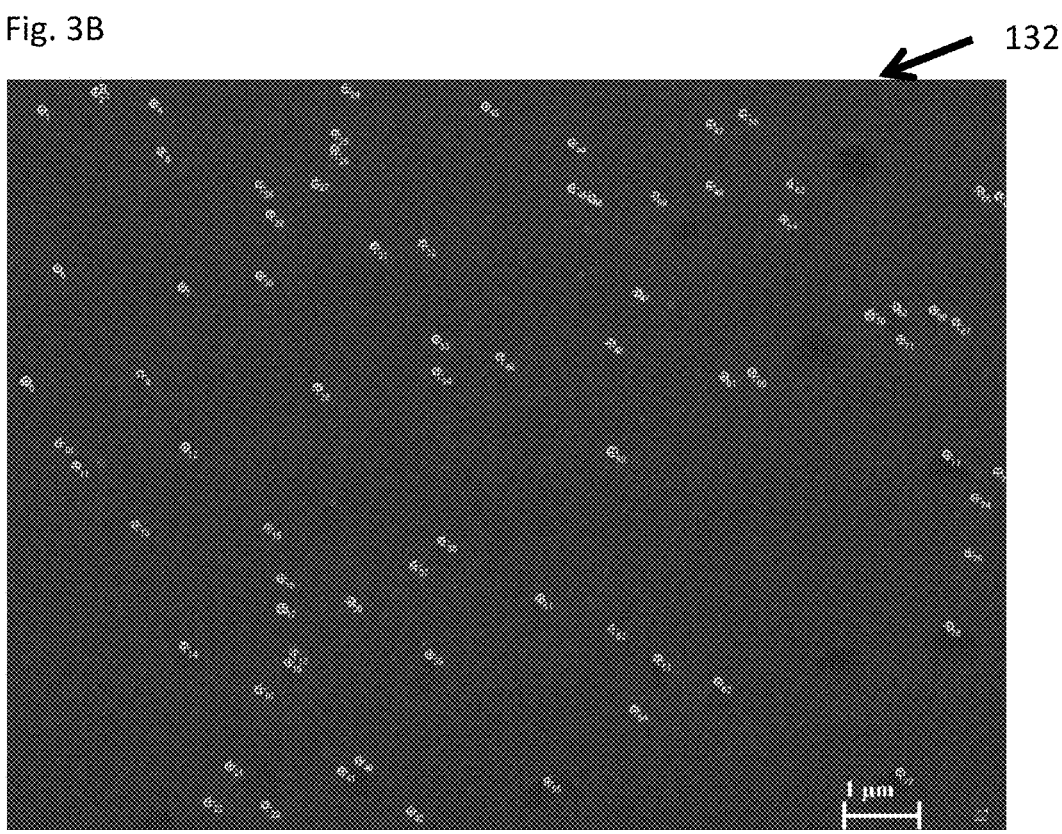
FIG. 3B is a detected and enumerated high magnification SEM image of polystyrene beads adhered to a poly-ether sulfone filter.
Figure 3C:
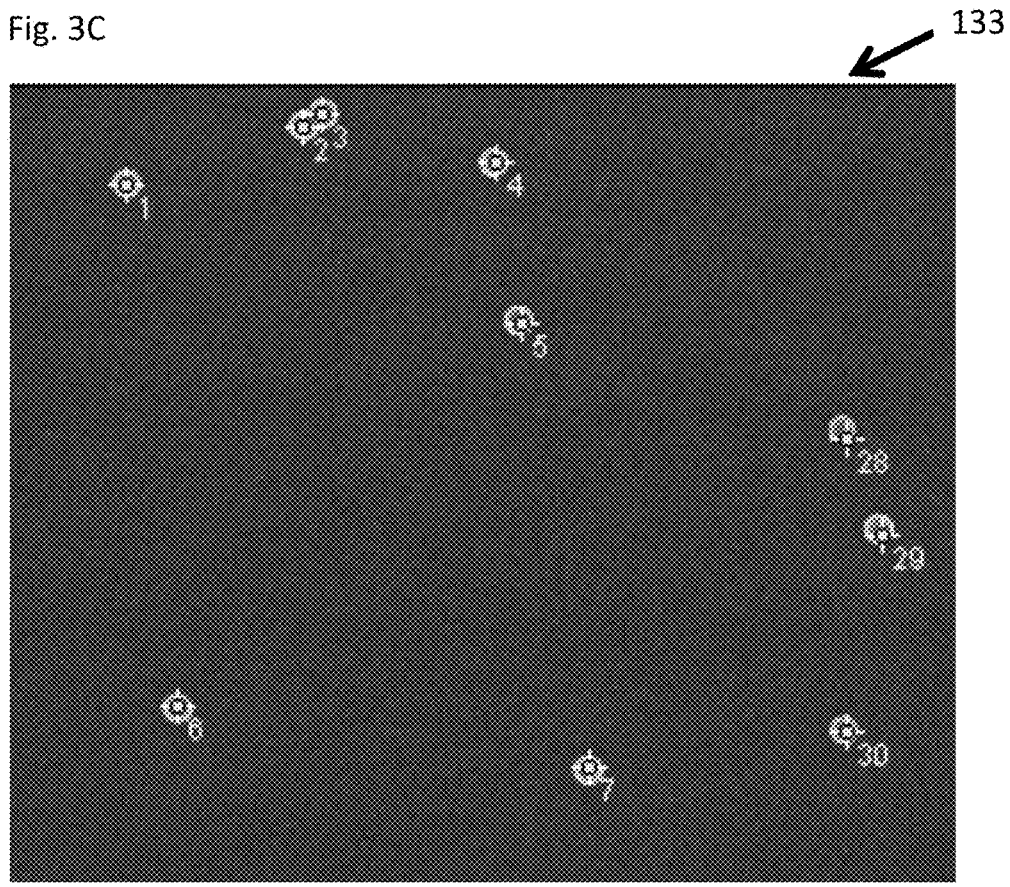
FIG. 3C is a close-up view of the SEM image of FIG. 3B above.

FIGS. 3A-3C are high magnification SEM images of polystyrene beads adhered to a poly-ether sulfone filter. FIG. 3A is an unprocessed image 130 and FIG. 3B is a detected and enumerated image 132. FIG. 3C is a close-up view 133 of the view of FIG. 3B and section 131 of FIG. 3A. In these example images, 77 particles were detected in a field of view of 131.47 µm$^2$. This corresponds to approximately 0.59 particles per µm$^2$. View 133 shows the numbered particles 1, 2, 3, 4, 5, 6, 7, 28, 29, 30.

Figure 4A:
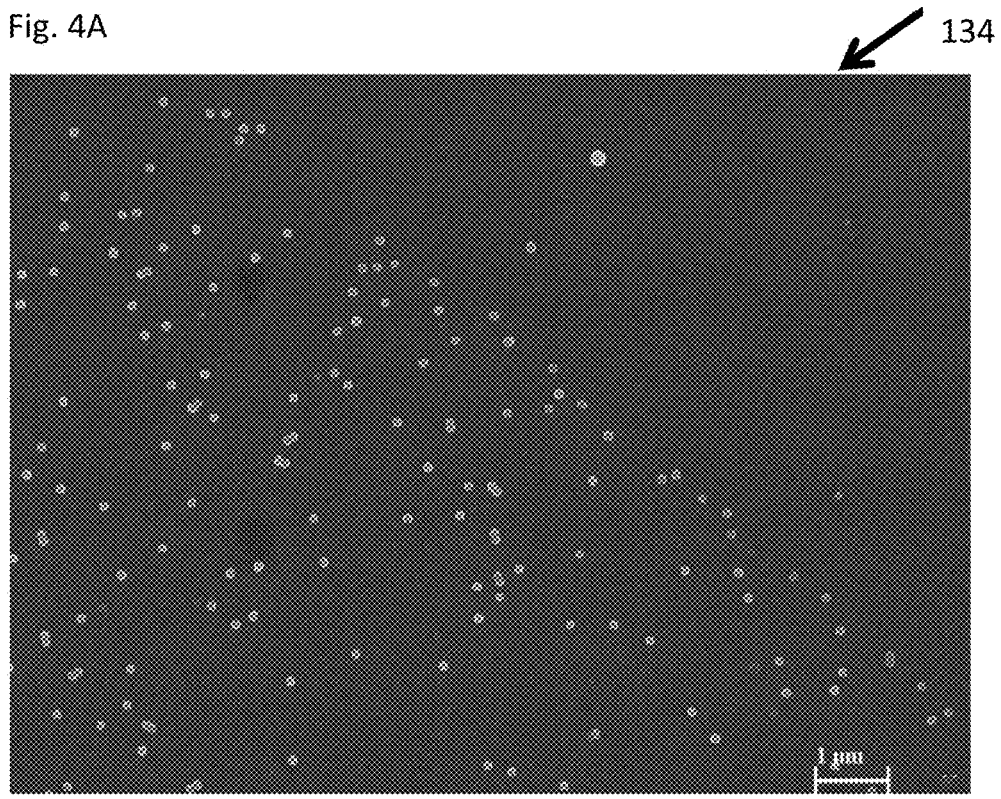
FIG. 4A is a schematic view of an edge of the droplet footprint image using SEM (primary electrons) at high magnification.
Figure 4B:
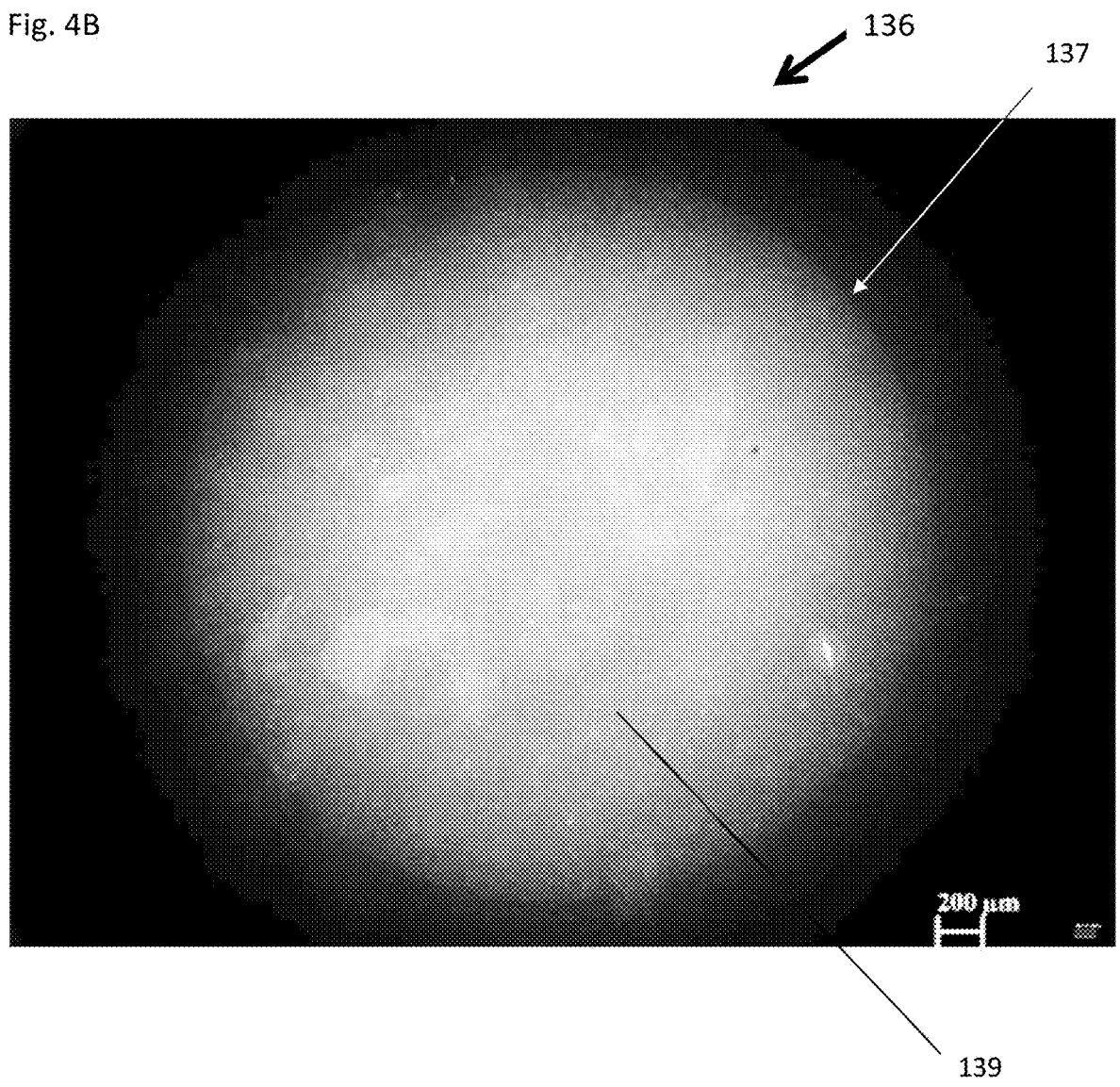
FIG. 4B is schematic view of an edge of the droplet footprint image using SEM (primary electrons) at low magnification.

FIGS. 4A-4B show the edge of the droplet footprint imaged using SEM (primary electrons). FIG. 4A show an image 134 at high magnification and FIG. 4B shows a footprint image 136 at low magnification. The location of the high magnification image 134, shown in FIG. 4A, is marked with a white arrow in FIG. 4B so that image 134 shows a portion of the entire footpring image 136. The edge of the droplet is well-defined with a negligable number of particles outside the footprint. At low magnification, the entire footprint 136 of the droplet is visualized and the area of the footprint can be precisely measured. In this example, the area of the footprint ($A_{total}$) was measured to 8.436 mm$^2$.

Figure 5A:
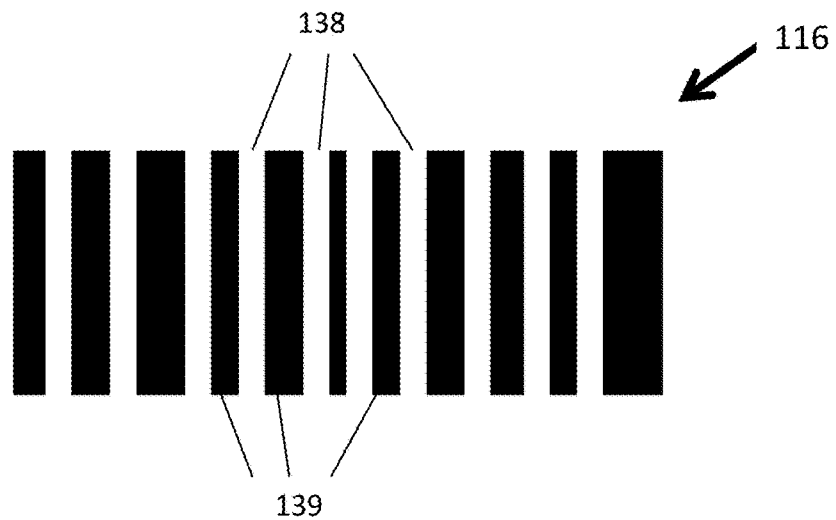
FIG. 5A is a cross-sectional schematic side view of the membrane of the present invention with open pores.
Figure 5B:
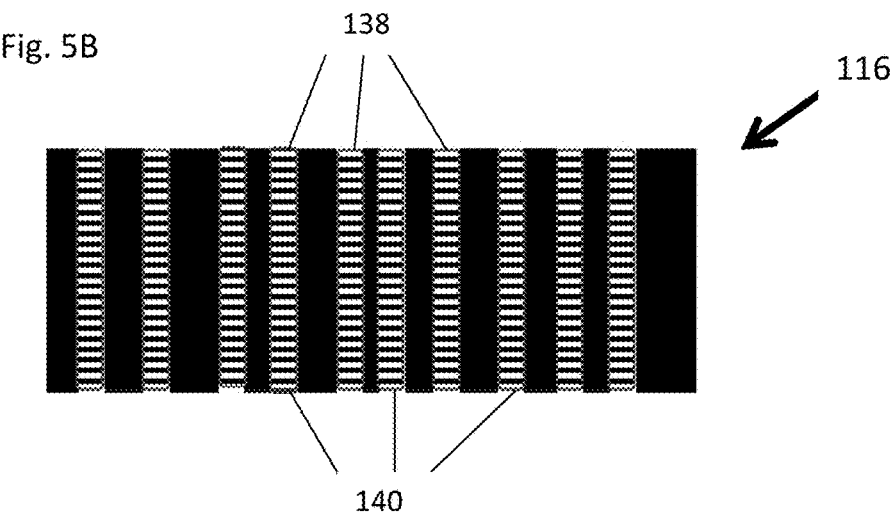
FIG. 5B is a cross-sectional schematic side view of the membrane shown in FIG. 5A but with sealed pores.

FIGS. 5A-5D are cross-sectional side views of the filter membrane 116 and describe the process of sealing the filter membrane 116 and then dissolving the sealant. In FIG. 5A, the filter membrane 116 has open pores 138, defined between elongate grid members 139 of the filter membrane 116, that extends through the filter membrane 116. In FIG. 5B, the pores 138 are filled with a sealant 140.

Figure 5C:
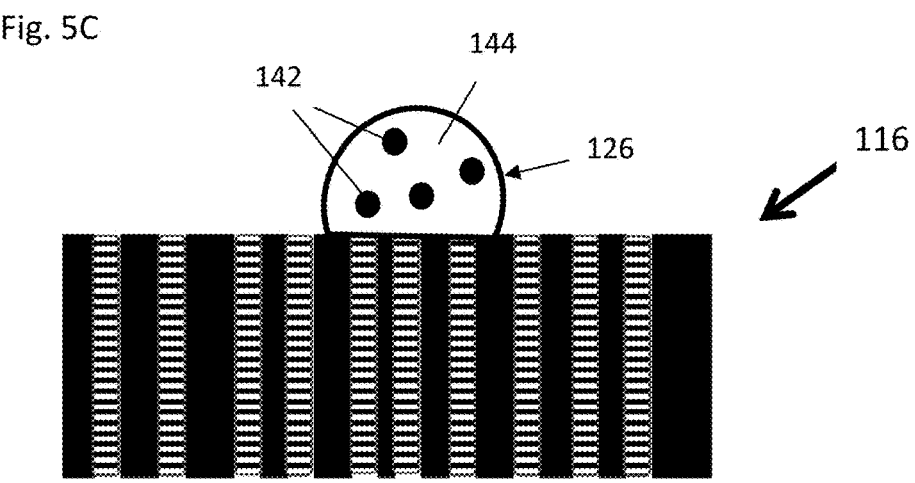
FIG. 5C is a cross-sectional schematic side view of the membrane of the present invention shown in FIG. 5B having a sample droplet deposited thereon.

In FIG. 5C, the sample droplet 126 of sample 124, that is a liquid 144 containing particles 142 to be analyzed, is deposited onto the filter membrane 116. Preferably, the droplet 126 is deposited onto the filter membrane 116 by using the injector 118 described above. Upon contact by droplet 126 with sealant 140, liquid 144 dissolves sealant 140 that is disposed immediately below droplet 126 so that the liquid 144 is absorbed and passed through the pores 138 only disposed below droplet 126. Because particles to be enumarated 142 have a size that is greater than pores 138 of the membrane, the particles 142 are deposited on top the filter membrane 116 while the liquid and any smaller contaminants 144 are absorbed or flows into the pores 138 below the droplet 126 as the sealant 140 in those pores are dissolved and the liquid 144 is subject to the suction from elongate chamber 128 of vacuum chamber 104 below filter membrane 116.

Figure 5D:
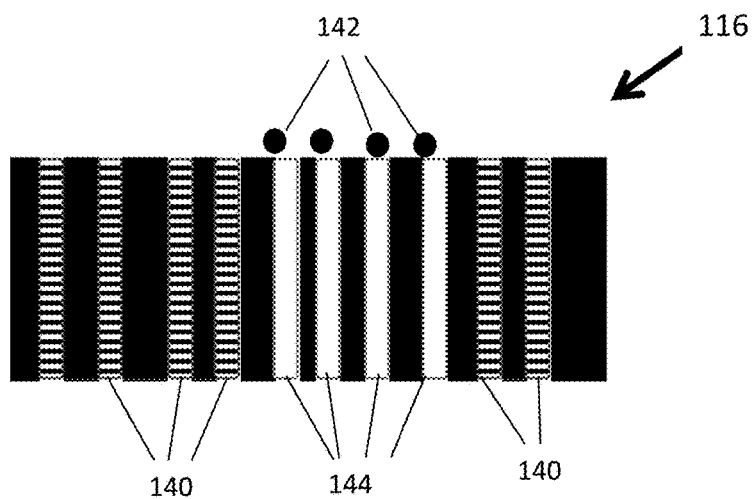
FIG. 5D is a cross-sectional schematic side view of the membrane shown in FIG. 5C having the droplet being absorbed into the membrane of the present invention.

Instead of filling the pores 138 with a sealant and using a vacuum chamber 104 to create a suction force, it is also possible to place a dissolvable layer, such as a poly-vinyl alcohol (PVA) layer, on top of the filter membrane 116 so that when the liquid 144 dissolves the layer, such as the PVA layer, the liquid 144 is urged by capillary forces to flow into the pores 138 and the particles 142 are left on top of the filter membrane 116 (as shown in FIG. 5D).

Figure 6:
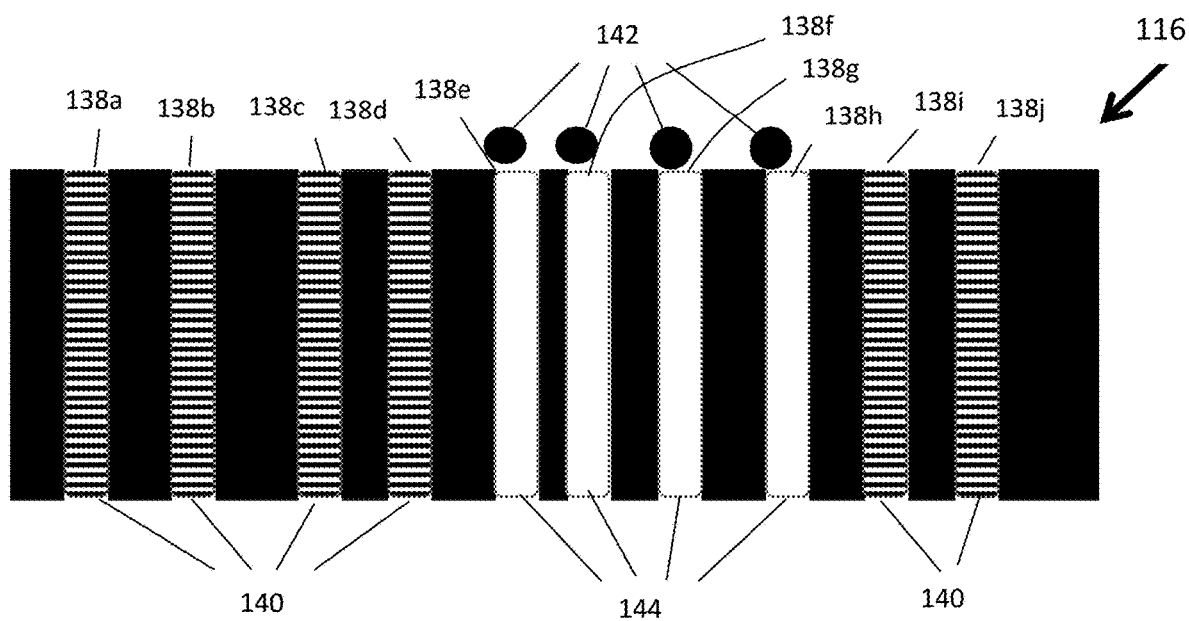
FIG. 6 is an enlarged view of FIG. 5D.

FIG. 6 is an enlarged view of the filter membrane 116 of FIG. 5D. The sub-visible particles 142 rest on the filter membrane 116 and the particles 142 are larger than the pores 138a-138j so they do not pass through the pores even if the pores are open and subject to suction from the vacuum chamber 104 (shown in FIG. 1). Pores 138a-d and 138i-j are still filled with sealant 140 since they have not been dissolved by the liquid 144 because they have not been in contact with the liquid 144 of sample droplet 126 (see FIG. 5C). More particularly, the diluent, such as a suitable buffer, in liquid 144 dissolves sealant 140. As indicated above, the diluent should be compatible with the specimen i.e. have minimal influence of the specimen morphology and aggregation state. The diluent should also have the property of dissolving the sealant. This is to make sure that the vacuum is only maintained at the footprint and so that the setup does not lose vacuum by "opening up" pores outside the area of interest. As the liquid 144 dissolves the sealant 140 disposed in pores 138e-138h, the liquid 144 fills pores 138e-138h to replace the sealant 140. This makes it easier to enumerate particles 142 because particles 142 are laying on top of filter membrane 116 and are well-distributed across the filter membrane 116.

EXAMPLE

Below is an illustrative example of method of preparing the filter membrane 116 according to the present invention.

1. A sample, containing sub-visible particles 142, such as micro-particles and/or nanoparticles, is prepared for enumeration by diluting the sample in series in an appropriate diluent (typically water, phosphate-buffered, HEPES-buffered, TRIS-buffered or Histidine-buffered saline) depending on the buffer conditions of each particular sample.

2. A fixation agent (typically glutaraldehyde or formaldehyde) and/or a stabilizing agent (typically sucrose or glycerol) can be introduced into the diluted sample solution 124, that also includes the sub-visible particles 142, to stabilize and preserve the structure of the particles and in some samples prevent undesirable aggregation of the particles 142. The fixation/stabilizing agents and the diluent correspond to liquid 144 and together with the particles 142 form the sample/specimen 124 and sample droplet 126. The fixation/stabilizing agents are used to prevent the particles 142 from being destroyed or damaged during handling and from undesirably adhering to one another which make it more difficult to later enumerate the particles 142.

3. The filter assembly 112 consists of the porous filter membrane 116 (typically made of poly-ether sulfone or polycarbonate) with pores 138 that have a defined pore size (typically 0 to 15 nm) and an openable filter cassette made of plastic or equivalent are used for separating the particles 142 from the liquid. A suitable filter assembly 112 is best shown in FIG. 2. In general, the filters are bought in bulk as single-use filters and thus need to be mounted on something. Some vendors also sell filter holders and these devices are originally made to be connected to a syringe and push the liquid through and thus not sucking the liquid through using vacuum. It is therefore necessary to mount the filter to a filter assembly to assure vacuum integrity. After some experimentation it was surprisingly realized that the filter could be mounted directly on the SEM support which saves time and avoids the critical steps of manually handling the specimen containing filters. It is conceivable that such an assembly can be inexpensively made and be sold as a SEM consumable.

4. The filter assembly 112 is mounted onto the top of the plastic vacuum chamber 104 which in turn is connected to the vacuum device 102 via tubing 106.

5. The vacuum in the vacuum chamber 104 is controlled by the 3-way Luer valve 108 and monitored by using the vacuum manometer 110. An automatic system using magnetic valves controlled by an electronic monitoring system can also be implemented.

6. The pores 138 in the filter membrane 116 are preferably sealed with sealant 140 such as glycine, PVA (polyvinyl alcohol) or equivalent prior to sample application of the sample droplet 126, as best shown in FIGS. 5B and 5C. It was surprisingly and unexpectedly discovered that by using sealant 140 in the filter membrane 116, the particles 142 inside droplet 126 were distributed more evenly (prior to removing the liquid 144 of the droplet 126) and there was no need to use a high vacuum force to reduce the risk of the droplet spreading out unevenly on the filter membrane. It should be noted that the distribution of the particles does not have to be the same at the outer periphery and as it is at the center. The pattern of the particle distribution can be determined by scanning the footprint 134/136 (see FIGS. 4A-4B) of the particle sample, disposed on the filter membrane, from the outer periphery or outer edge 137 of the foot print 136 towards the center 139 of the footprint of the particle sample. If the scanned portion of the particle sample shows a certain pattern of distribution of particles, it can be reliably assumed that the same particle distribution pattern applies around the entire circular-shaped particle sample footprint 136 partly because the particles were given time to settle before the sealant 140 is dissolved by the liquid in the droplet 126. Because the droplet 126 is first deposited onto the sealed filter membrane 116 the outer edge 137 of footprint 136 of the droplet 126 becomes relatively distinct or sharp which is important in order to determine where to start the enumeration and scanning towards the center 139 of the circular-shaped particle sample or footprint 136 deposited on the dissolved filter membrane 116. It was unexpectedly discovered that the advantages of the relatively even distribution of the particles on the filter membrane outweighed the drawbacks of having to remove the sealant to permit the liquid in the droplet to flow through the filter membrane before starting the enumeration of the particles. Any uneven or non-distinct periphery of the footprint of the droplet on the filter membrane makes it more difficult to determine the footprint thereof and know which area is to be analyzed in order to count all the particles in the droplet. By applying the sample droplet 126 onto the filter membrane 116, with all the pores 138 being sealed by sealant 140, the particles 142 are evenly distributed inside droplet 126 as the droplet 126 spreads out on the sealed top surface of filter membrane 116. The requirement of having to dissolve the sealant 140 first slows down the flow-through of the liquid 144 through the pores 138. By not using the sealant 140, the liquid 144 of the droplet 126 would immediately start to flow through the pores 138 and because the droplet 126 is thickest at the center and thinner at its periphery more particles 142 tend to be located in the middle of the droplet. This often results in an uneven distribution of the particles onto the filter membrane and the outer edge of the foot print of the particles sample is not clear. It should be noted more particles are not always located in the middle of the droplet because some specimens may have a tendency to concentrate towards the air-water interface. It is generally difficult to exactly foresee how different samples behave and distribute.

Since the entire footprint 136 of the sample droplet 126 is used to calculate the particle concentration of particles 142, the droplet 126 should not touch the inner edge of the filter holder of filter membrane 116. Thus, it is important that only a defined part of the filter membrane 116 is covered with the sample droplet 126. This is to make sure that all the particles 142 in the droplet 126 are enumerated or counted. Also, the position of sample droplet 126 should be aligned with cavity 129 and channel 128 defined inside stub 120. Without pretreatment of the filter membrane 116 with sealant 140, the surrounding filter pores, i.e. pores 138a-138d and 138i-138j in FIG. 6, remain open and air flows around the droplet 126 and through the filter membrane 116 so that the sample droplet 126 does not absorb and becomes filtered fast enough to get a good sample distribution of the particles 142. In other words, the use of the sealant 140 has the advantage of creating a more distinct outer periphery 137 of the footprint 136 of droplet 126 when liquid starts to dissolve sealant 140 that is deposed below droplet 126. Without the use of sealant 140 there is not enough time for the particles 142 to be evenly distributed inside droplet 126 since the liquid 144 immediately starts to flow through the pores 138 without giving the particles 142 time to settle and be evenly distributed inside droplet 126. One very important feature of sealant 140 is thus to create a vacuum condition so that a defined specimen footprint is formed. More particularly, without the treatment of the sealant 140 according to the present invention, the droplet 126 undesirably dries through diffusion and evaporation. This results in a highly uneven particle distribution due to the drying effects. It was surprisingly discovered that the undesirable evaporation may cause osmotic effects potentially causing particle disruption and crystal formation due to increased salt concentration in the remaining droplet. Additionally, this obscures the particle detection and enumeration caused by broken particles and particles that are hidden by salt precipitates. In the present invention, when applying the sample droplet 126 onto the sealed filter membrane 116, the liquid 144 in the sample droplet 126 slowly dissolves the sealant 140 to open the pores 138e-138h disposed underneath the droplet 126. Consequently, the liquid 144 is rapidly drawn through the pores 138e-138h of filter membrane 116 by the vacuum, resulting in a good sample distribution of particles 142 on the top surface of filter membrane 116.

7. Before applying the sample droplet 126 onto the filter membrane 116, the vacuum device 102 is activated and the pressure in the vacuum chamber 104 is lowered to create suction on the filter membrane 116. The vacuum in the vacuum chamber 104 ensures that the liquid 144 of droplet 126 is absorbed evenly on the filter membrane 116. The combination of the usage of the sealant and the vacuum results in an even distribution of particles 142 across the footprint 136 on the filter membrane 116.

8. A suitable volume (typically 5 µl) of the sample droplet 126 is applied on the porous and sealed filter membrane 116. As indicated above, it is important that the diameters of the particles 142 are greater than the diameter of pores 138 of filter membrane 116 and that the droplet 126 does not touch the edges of the filter mount. A higher volume than 5 µl can be applied by using an injection system where either multiple drops or larger volumes are applied on the same position on the filter membrane 116. In general, the use of larger volumes minimizes the sampling error and allows the analysis of less concentrated samples.

9. The sample droplet 126 is absorbed on the filter membrane 116 for typically 60 seconds under vacuum pressure provided by vacuum chamber 104. The exact pressure values may have to be adjusted partly depending on pore size, sample type, volume, purity and viscosity.

10. After absorption, the filter membrane 116 may be detached from the filter assembly 112 mounted onto the SEM alumina stub 120 (typically by using an adhesive and conductive carbon tape 122).

11. The filter membrane 116, with bound particles 142 placed thereon, may then be sputter coated by for example a thin film of carbon (typically 20 nm thick) using a carbon evaporator at a suitable chamber pressure typically $1 \times 10^{-5}$ mbar. The sputter coating improves the conductivity of the filter membrane 116; increases the signal to noise ratio of the filter membrane 116 and reduces the electron beam damage and charging effects. This technique is often necessary to use in order to image a filter material using a SEM. It may be unconventional to use carbon coating but it provides higher resolution SEM imaging compared to the larger grain size of metal sputtering.

12. The filter membrane 116 may be transferred to the SEM and the signal from scattered primary electrons (using an in-lens detector) or secondary electrons (such as by using a SE2 detector) is recorded both at low to cover the entire footprint and high magnification (typically 10,000 to 30,000) for enumeration. If a reference standard with a different secondary electron signature is used (albeit not necessary to determine the particle concentration) the particles of interest can be distinguished from the reference particles by combining intensity information from different detectors (such as in-lens and SE2 detectors).

13. The low magnification images 136 (see FIG. 4B) are used to define the size of the footprint of the droplet and the overall specimen distribution while the high magnification images are used to determine the particle enumeration.

14. The high magnification images, such as image 134, are acquired across the sample footprint starting from the edge 137, through the center 139 and to the opposite edge of the droplet in order to minimize any effect of differences in particle distribution across the footprint of the droplet.

15. From the low magnification images, such as image 136, the area of the sample footprint ($A_{total}$) is calculated by tracing the edge of the footprint. The encircled pixels are counted and the number counted is multiplied with the pixel size.

16. From the high magnification images, the particles 142 are detected and counted. This procedure can be performed through manual marking or automated marking by using suitable software such as Vironova's proprietary software Analyzer or any other appropriate image analysis software. The average number of particles per area unit ($n/A_{FOV}$) is calculated from the image dataset.

17. The number of particles per mL in the particle sample is, preferably, calculated by using the following formula:

$$C = A_{total} \times \frac{n}{A_{FOV}} \times df \times \frac{1000 \text{ µl}}{V \text{ µl}}$$

Where C is the concentration of particles, df is the dilution factor and V is the applied volume of sample. It may also be possible to use a formula that takes into account that the particle distribution may vary from the periphery of the particle sample as the sample is scanned towards the center thereof.

In summary, the particle quantitative scanning electron microscopy (pqSEM) technique of the present invention is a high-precision direct particle detection and enumeration technique. An important feature of the present invention is that the direct detection does not depend on the affinity between a probe and the specimen which many existing conventional techniques do. All parameters, such as the dilution factor, the applied volume, the footprint of the droplet can be controlled and the number of particles per area unit can be directly measured while minimizing the error from approximations and assumptions. Moreover, the resolving power of the pqSEM permits detection of individual sub-visible particles within clusters and two populations of particles of different sizes or other morphological features can be enumerated from the same sample. The particles and the footprint from the high-contrast images generated by the pqSEM technique of the present invention can readily be detected by using automated image analysis. This provides the means for rapidly collecting large datasets and producing robust statistical results.

Figure 9:
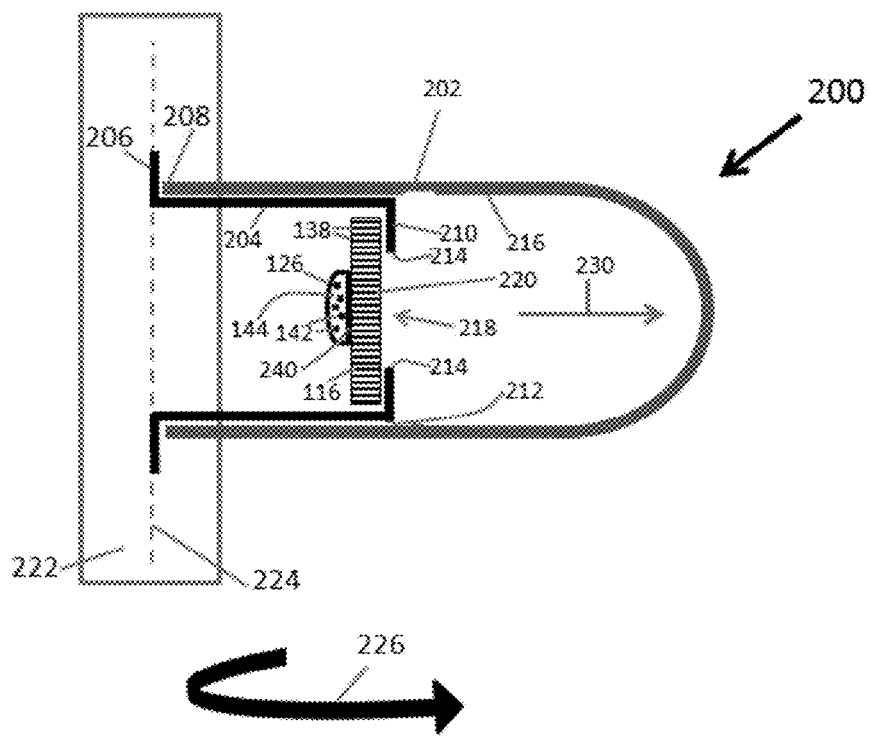
FIG. 9 is a cross-sectional schematic side view of an alternative embodiment of the present invention in a horizontal rotating position.

FIGS. 7-9 show cross-sectional views of an alternative embodiment of a rotatable container arrangement 200 of the present invention. The arrangement 200 illustrates an alternative way of forcing liquid through the filter membrane in order to define and distinctly limit, in a controlled manner, the region of the particles on the membrane. It is thus desirable to use a force that drives the liquid straight down through the pores 138 so that the remaining particles 142 on top of the filter membrane 116 are deposited evenly in the region 240 that is substantially covered by the sample droplet 126.

The force through the membrane may include suction forces, capillary forces, centrifugal forces or any other suitable force. It is also important that the sealant 140 is sufficiently dissolved in the pores 138 to allow the liquid 144 to flow through the pores 138 and to prevent the liquid and particles 142 from uncontrollably floating sideways on top of the filter membrane 116. The arrangement 200 does not require any pre-mounting of the filter or the use of a vacuum source to suck the liquid through the pores of the filter membrane, as described above regarding FIGS. 1-6. It is to be understood that the pores 138 in the filter membrane 116 are not necessarily straight down but includes a network of pores that are not straight.

More particularly, an elongate hollow container 202, such as a suitable test tube, is placed in a vertical position (best shown in FIG. 7). The container 202 has a membrane support 204 inserted inside the container 202. The membrane support 204 has an upper support segment 206, that rests upon an upper surface 208 of the container 202, and a lower support segment 210, provides support for the filter membrane 116. The lower support segment 210 extends around an inner periphery 212 inside the container 202. The lower support segment 210 has an outer portion 214 extending inwardly from an inside wall 216 of the container 202 so that an opening 218 is defined inside the outer portion 214 and below a central portion 220 of the membrane 116. Preferably, the opening 218 and central portion 220 are wider than a region 240 covered by the sample droplet 126.

More particularly, the filter membrane 116 has the samplet droplet 126 placed on top of the filter membrane and the droplet contains particles 142 and a liquid 144. The opening 218 is positioned below the central portion 220 of the membrane 116 and the sample droplet 126 when the container 202 is in the vertical position, as shown in FIG. 7. The details and operation of the filter membrane 116, droplet 126, particles 142 and liquid 144 are described with reference to FIGS. 5A-5D and apply to FIGS. 7-9 also. Preferably, the filter membrane 116 and the droplet 126 shown in FIGS. 7-9 are identical to the filter membrane 116 and droplet 126, shown in FIGS. 5A-5D.

The filter membrane 116 rests upon the lower support segment 210 while the upper support segment 206 rests upon the upper surface 208 of the container 202 so that the membrane support 204 hangs inside the container 202 and the membrane 116 on the inwardly directed lower support segment 210 so that the central portion 220 of the membrane 116 is aligned with the opening 218 that is formed inside the outer portion 214. Instead of having one membrane support 204 that extends around the inside periphery 212 of the container 202 it is also possible to use several membrane-supports that only partially extends around the inside the periphery 212 of the container 202.

An important feature of the arrangement 200 is that different force/pump/drivers may be used to push the liquid through the membrane 116. More particularly, there are alternative ways of forcing the liquid 144 in the droplet 126 through the pores 138 of the membrane 116 in a defined or distinct region 240 just below the droplet 126 i.e. at the central portion 220. It is desirable that the region 240 is clearly defined so that it is distinctly known where the remaining particles 142 are located. A centrifugal force 230 may be created by rotating the container 202 containing the membrane 116 with the sample droplet 126 placed on top of the membrane 116, as described above. The container 202 is attached to a rotating device 222, such as a swing-out rotor, so that the container 202 rotates around a rotational axis 224, as indicated by arrow 226. While the container 202 is rotated, the container 202 is gradually moved from the vertical position, shown in FIG. 7, via the intermediate position, shown in FIG. 8, to the horizontal position, shown in FIG. 9. The rotational speed gradually increases as the container 202 is moved to the horizontal so that the full rotational speed is not used until the container 202 is in the horizontal position shown in FIG. 9 and the centrifugal force acts on the liquid to force the liquid straight through the membrane in a way similar to that of a vacuum described above.

When the liquid 144 dissolves the sealant 140 disposed in the pores 138 of the membrane 116, as described in detail in connection with the description of FIGS. 5A-5D, the centrifugal force 230 that is formed when the container 202 is rotated around axis 224, forces the liquid 144 through the pores 138 while the particles 142 rest on top of the pores 138 (as shown in FIG. 5D). The sealant 140 may be glycine, PVA (poly-vinyl alcohol) or any other suitable sealant material that, preferably, is hydrophilic.

Figure 10:
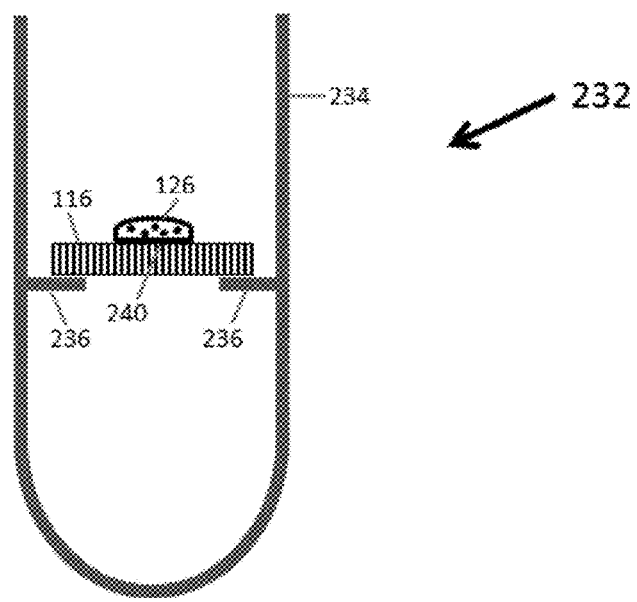
FIG. 10 is a cross-sectional schematic side view of yet an alternative embodiment of the present invention in a vertical position.

FIG. 10 shows an alternative arrangement 232, that has an alternative container 234, that operates in the same way as the arrangement 200, described in connection with FIGS. 7-9, so only the main differences are therefore described herein. The container 234 has an inwardly directed support member or shelf 236 attached to an inner wall 238 of the container 234 that extends around an inner periphery of the container 234.

Figure 11:
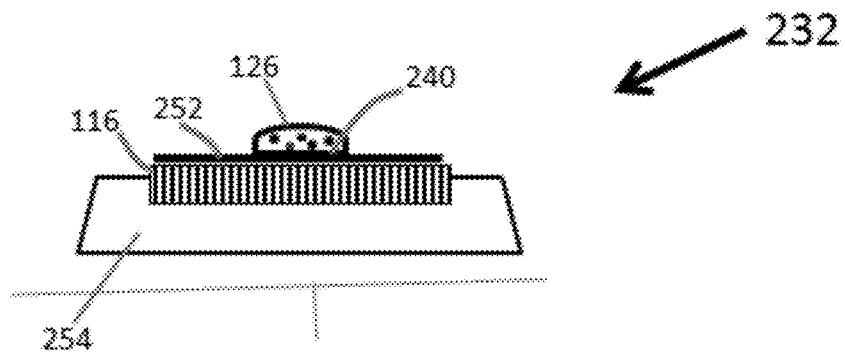
FIG. 11 is a cross-sectional schematic side view of yet an alternative embodiment of the present invention.

FIG. 11 shows an alternative arrangement 250 that has the sample droplet 126 resting on a dissolvable (such as PVA (poly-vinyl alcohol)) layer or film 252 that is placed on top of the membrane 116 that, preferably but not necessarily, rests on a filter paper 254. When arrangement 250 is used together with a rotational force, the filter paper 254 is not needed. Instead the PVA film or any other suitable film and the membrane are placed in the rotation container 234 or 200. For arrangement 250 with the filter paper 254, instead of having a dissolvable sealant disposed inside the pores 138 of the membrane 116, the sealant may instead be in the form of the PVA layer 252 that is disposed on top of the membrane 116 but below the sample droplet 126 so that the droplet 126 rests on the PVA layer 252 instead of on the membrane 116. It is to be understood that the pores 138 may instead be filled with a suitable dissolvable sealant, such as glycine or PVA, so that the arrangement 250 is used without the PVA layer 252. This may be done by first dissolving PVA or glycine in water and let the dissolved solution flow into and fill the pores 138 of the membrane 116 and then let the water evaporate so that the solid PVA or glycine remains in the pores 138 to fill and seal the pores 138. It may also be possible to heat the PVA or glycine to make it flowable before the sealant flows into to the pores where it cools and solidifies. PVA may thus be used either in the form of a thin film/layer disposed on top of the membrane 116 or as a solid sealant that is used to fill the pores 138. As described above, the liquid 144 dissolves the PVA layer 252 and the capillary forces that are formed in the open empty pores 138 urge the liquid 144 to flow through the pores 138. PVA is a hydrophilic dissolvable plastic which has the same function as the glycine of sealant 140 in the above-described embodiments related to FIGS. 1-6. More particularly, the liquid 144 in sample droplet 126 dissolves only the region 240 of the PVA layer 252 upon which the droplet 126 rests. Capillary forces urge the liquid 144 through the pores 138. In other words, when the region 240 of the PVA layer 252 is dissolved by the liquid 144 capillary forces in the open empty pores 138 drive the liquid 144 through the dissolved region of the PVA layer 252 and through the pores 138. To provide additional suction or capillary forces, the filter paper 254, that includes many pores that creates a suction force, is preferably placed immediately below the membrane 116. Preferably, the membrane 116 should be thin enough and the pores 138 should be big enough so that when the PVA layer 252 is dissolved by the liquid 144, the liquid 144 is urged to flow sufficiently far into the pores 138 when subject to the capillary forces of the pores 138 so that the liquid 144 eventually comes into contact with the filter paper 244 that triggers the enhanced suction of liquid 144 through the pores 138 and into the filter paper 244. This enhanced suction prevents the liquid 144 from flowing sideways or in uncontrollable directions on top of the membrane 116. An important feature of the arrangement 250 is that it is not necessary to rotate the arrangement, as described in FIG. 7-9, to urge the liquid through the pores 138 of the membrane 116. Instead the arrangement 250 relies on the capillary forces created in the open pores 138 and the filter paper 254 to urge the liquid 144 through the pores 138 of the membrane 116. Preferably, the filter paper 254 should have a dimension that is greater than the region 240 so that the filter paper 254 can create a suction force in all the pores 138 through which the liquid 144 flows. The filter paper 254 should also be large enough to create sufficient suction force to drive the liquid through the pores and be able to absorb all the liquid 144 of the sample droplet 126. The required size of the filter paper thus partly depends on the size of the sample droplet 126. Also, the PVA layer 252 should be dimensioned to be at least as big as the region 240 i.e. the surface area that contains pores in which the liquid 144 has dissolved the sealant 140 or contains pores that are disposed below PVA layer 252 that the liquid 144 has dissolved. Instead of using the filter paper 254 as a suction source together with the PVA layer 252, it is possible to use a pump or another source to create a vacuum below the filter membrane 116.

One advantage of the methods described in FIGS. 7-11 is that it is not necessary to seal every pore in the membrane 116 which is the case when vacuum is applied below the membrane (as described in FIGS. 1-6) because if not all the pores are sealed then air is sucked in by the vacuum through the unfilled pores.

Figure 12:
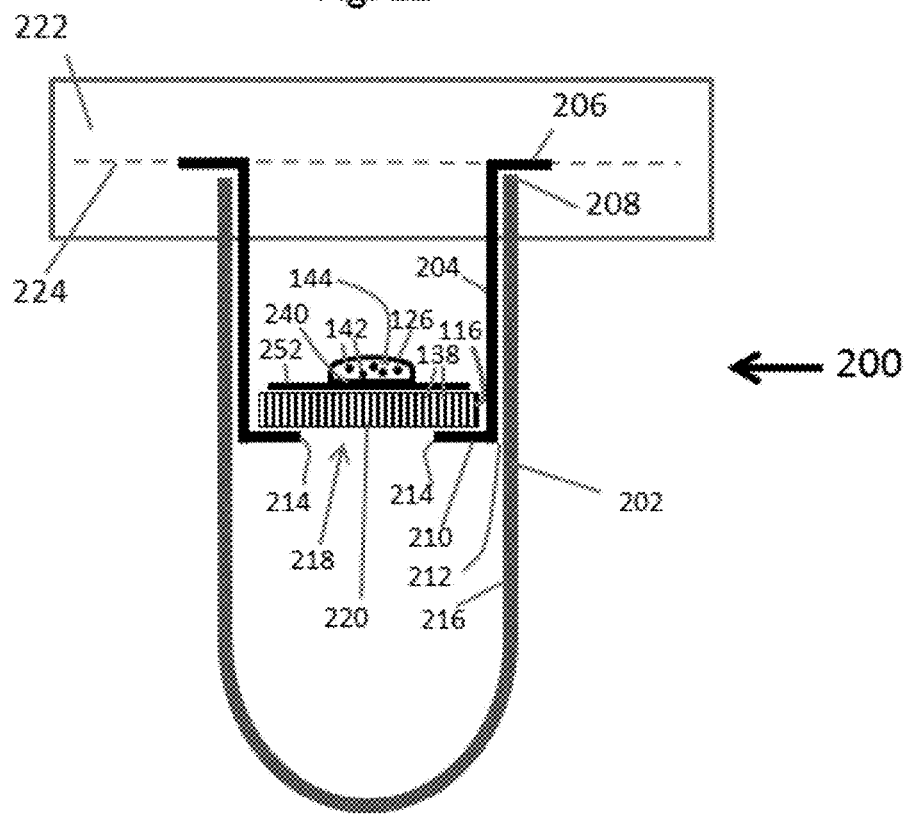
FIG. 12 is a cross-sectional schematic side view of yet an alternative embodiment of the present invention in a vertical position.

FIG. 12 is a cross-section view that is virtually identical to FIG. 7 except that it has sealant layer 252, such as a PVA layer, placed between the sample droplet 126 and the filter membrane 116, instead of sealing the pores 138 with a sealant 140, as described in FIG. 7. The liquid in the droplet 126 dissolves the region 240 immediately below the droplet 126, as described in connection with FIG. 11. The embodiment shown in FIG. 12 is thus a mixture of the embodiment shown in FIG. 7 and the embodiment shown in FIG. 11. All other aspects of the embodiment shown in FIG. 7 are identical to the embodiment shown in FIG. 12 and are therefore not described in detail here.

While the present invention has been described in accordance with preferred compositions and embodiments, it is to be understood that certain substitutions and alterations may be made thereto without departing from the spirit and scope of the following claims.

We claim:

1. A method for quantification of sub-visible particles, comprising:
    providing a filter membrane having a plurality of pores defined therethrough;
    positioning a dissolvable sealing layer on the filter membrane and placing a filter paper below the filter membrane;
    applying a sample droplet, containing liquid and sub-visible particles, onto the sealing layer;
    the liquid dissolving a region of the sealant layer disposed below the sample droplet;
    the liquid flowing through the pores disposed below the region and into the filter paper, the sub-visible particles remaining on top of the filter membrane;
    the filter paper providing a suction force to urge the liquid to flow through the pores in the region; and
    the sub-visible particles being enumerated in an electron microscope.

2. The method of claim 1 wherein the method further comprises providing a poly-vinyl alcohol (PVA) layer on top of the filter membrane.

3. A method for quantification of sub-visible particles, comprising:
    providing a container containing a filter membrane having a plurality of pores defined therethrough;
    sealing the pores with a sealant;
    applying a sample droplet, containing liquid and sub-visible particles, onto the filter membrane;
    the liquid dissolving the sealant in pores disposed below the sample droplet;
    rotating the container to create a centrifugal force;
    the centrifugal force urging the liquid through the pores in which the liquid has dissolved and the sub-visible particles remaining on top of the filter membrane; and
    the sub-visible particles being enumerated in an electron microscope.

4. The method of claim 3 wherein the method further comprises resting the filter membrane on a support disposed inside the container.

5. The method of claim 3 wherein the method further comprises placing the sample droplet on the filter membrane when the container is in an upright position and gradually moving the container to a horizontal position while rotating the container.

6. The method of claim 5 wherein the method further comprises the step of rotating the container about a rotation axis at a top of the container.

7. The method of claim 3 wherein the method further comprises the step of the liquid only dissolving the sealant in the pores disposed immediately below sample droplet while adjacent pores remain sealed with the sealant.

8. The method of claim 3 wherein the method further comprises the step of using poly-vinyl alcohol (PVA) as the sealant.

9. The method of claim 3 wherein the method further comprises applying the sample droplet onto the filter membrane without the sample droplet touching any outside edge of the filter membrane.

10. A method for quantification of sub-visible particles, comprising:
    providing a container containing a filter membrane having a plurality of pores defined therethrough;
    positioning a dissolvable sealing layer on the filter membrane;
    applying a sample droplet, containing liquid and sub-visible particles, onto the sealing layer;
    the liquid dissolving a region of the sealant layer disposed below the sample droplet;
    rotating the container to create a centrifugal force;
    the centrifugal force urging the liquid through the pores in the region which the liquid has dissolved and the sub-visible particles remaining on top of the filter membrane; and
    the sub-visible particles being enumerated in an electron microscope.

11. The method of claim 10 wherein the method further comprises the step of using poly-vinyl alcohol (PVA) as the sealant layer.

* * * * *